United States Patent [19]

Higashii et al.

[11] Patent Number: 5,659,051

[45] Date of Patent: Aug. 19, 1997

[54] PROCESS OF PRODUCING 2-CYANO-4-OXO-4H-BENZOPYRAN COMPOUNDS

[75] Inventors: Takayuki Higashii, Yokohama; Hideki Ushio; Yukari Fujimoto, both of Takatsuki; Tsutomu Matsumoto, Kyoto; Masayoshi Minai, Moriyama; Katsuichi Yasunaga, Suita; Hiroshi Sogabe, Toyonaka; Takahiro Kotera, Ibaraki, all of Japan

[73] Assignee: Sumitomo Chemical Company, Limited, Osaka-fu, Japan

[21] Appl. No.: 273,119

[22] Filed: Jul. 11, 1994

[30] Foreign Application Priority Data

| Jul. 13, 1993 | [JP] | Japan | 5-173333 |
| Jul. 14, 1993 | [JP] | Japan | 5-174439 |
| Jul. 19, 1993 | [JP] | Japan | 5-178065 |
| Jul. 21, 1993 | [JP] | Japan | 5-180250 |
| Aug. 23, 1993 | [JP] | Japan | 5-207498 |
| Nov. 1, 1993 | [JP] | Japan | 5-273669 |

[51] Int. Cl.$^6$ .......................... C07D 311/24
[52] U.S. Cl. .................. 549/401; 549/402; 549/404; 549/405; 549/407; 558/311; 558/312; 558/382; 564/134
[58] Field of Search .................. 549/401, 402, 549/404, 405, 407; 558/311, 312, 382; 564/134

[56] References Cited

U.S. PATENT DOCUMENTS 3,839,339  10/1974  Ellis et al. .................. 260/308 D

FOREIGN PATENT DOCUMENTS

| 794639 | 1/1973 | Belgium . |
| 2185409 | 5/1973 | France . |
| 2208674 | 12/1973 | France . |
| 2105191 | 8/1971 | Germany . |
| 1428676 | 3/1976 | United Kingdom . |
| 1457256 | 12/1976 | United Kingdom . |
| 1457255 | 12/1976 | United Kingdom . |
| 1457254 | 12/1976 | United Kingdom . |
| 1488707 | 10/1977 | United Kingdom . |

OTHER PUBLICATIONS

Ellis et al, "Journal of Medicinal Chemistry", 1972, vol. 15, No. 8, pp. 865–867.
Ciattini et al, "Synthesis", 1983, pp. 311–312.
Journal of Med. Chem., vol. 31, No. 1, 1988, pp. 84–90, Hisao Nakai et al. "New Potent Antagonists of Leukotriene $C_4$ and $D_4$1. Synthesis and Structure–Activity Relationship.".
Campagna et al, "Tetrahedron Letters", No. 21, pp. 1813–1816, 1977.

*Primary Examiner*—Ba K. Trinh
*Attorney, Agent, or Firm*—Birch, Stewart, Kolasch & Birch, LLP

[57] ABSTRACT

There is disclosed a process of producing a 2-cyano-4-oxo-4H-benzopyran compound of the general formula (2):

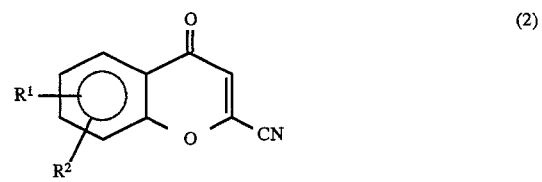

wherein $R^1$ and $R^2$ are independently hydrogen, halogen, hydroxy, $C_1$–$C_5$ alkyl, $C_1$–$C_5$ alkoxy, nitro or a group of the RCONH wherein R is $C_1$–$C_{20}$ alkyl, phenyl, phenyl-substituted ($C_1$–$C_{20}$) alkyl, phenyl ($C_1$–$C_{20}$)alkoxyphenyl or ($C_1$–$C_{20}$) alkoxyphenyl. This production process is characterized in that a carboxamide of the general formula (1):

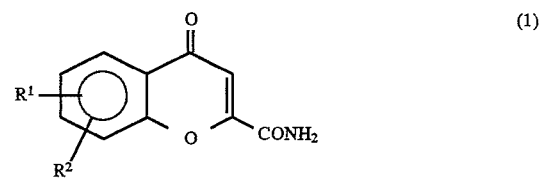

wherein $R^1$ and $R^2$ are each as defined above, is reacted with a dehydrating agent in the presence of a pyridine compound of the general formula (4):

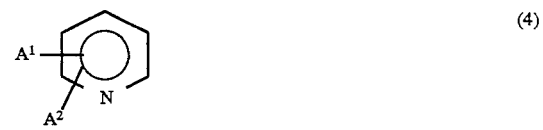

wherein $A^1$ and $A^2$ are independently hydrogen or $C_1$–$C_5$ alkyl. If the final product cannot be obtained as crystals having good filtration properties by ordinary treatments, a novel technique as disclosed herein can provide such crystals by dissolving the reaction product in an organic solvent insoluble or slightly soluble in water; pouring the resultant solution into water; and removing the organic solvent by distillation with stirring to effect the crystallization of the final product.

13 Claims, No Drawings

PROCESS OF PRODUCING 2-CYANO-4-OXO-4H-BENZOPYRAN COMPOUNDS

FIELD OF THE INVENTION

The present invention relates to an industrially favorable process of producing 2-cyano-4-oxo-4H-benzopyran compounds which can be used as intermediates for the production of some kinds of 2-(tetrazol-5-yl)-4-oxo-4H-benzopyran derivatives. It has been known that these derivatives exhibit at least partial competition with one or more of leukotrienes, particularly leukotrienes C and D, and therefore have pharmacologically effective characteristics (see, e.g., Prostaglandins, Leukotrienee Essent. Fatty Acids, 48(3), 241, 1993).

BACKGROUND OF THE INVENTION

As the process of producing 2-cyano-4-oxo-4H-benzopyran compounds, for example, there has been known a process using 2-hydroxyacetophenone compounds as the starting material (see, e.g., Journal of Medicinal Chemistry, 1972, Vol. 15, No. 8, which is shown in the following reaction scheme:

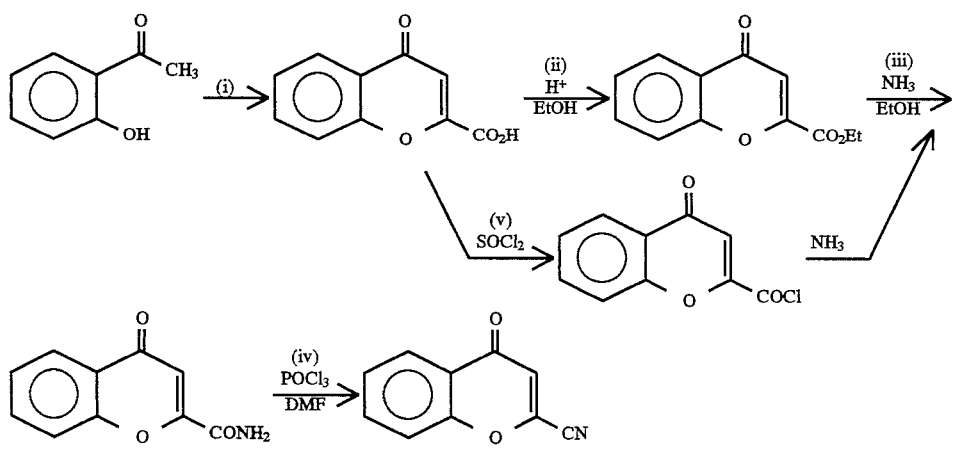

In the above process, however, since an alcohol is used as the solvent in the second and third steps, and ammonia is used in the third step, serious problems will occur that a great amount of Waste water containing the alcohol of high concentration or containing ammonia has to be discharged in the production on an industrial scale.

In the fourth step, ordinary conditions for the dehydration of carboxamides are used; for example, (a) phosphorous oxychloride, phosphorous pentoxide or the like is used as the dehydrating agent and DMF, pyridine or a mixture thereof is used as the solvent; or (b) phosgene is used as the dehydrating agent and a hydrocarbon such as dichloromethane or dichloroethane is used as the solvent.

However, the conditions (a) has a disadvantage in that complicated procedures are necessary for the removal of the solvent from the waste water because DMF or pyridine used as the solvent is soluble in water and such a solvent gives a high load on the waste water. Also the conditions (b) are not always satisfactory for the production on an industrial scale because relatively high temperatures are required therefor.

In the above reaction scheme, it has been known that the following side reaction will be caused in the process (v) which is conducted by way of acid chlorides.

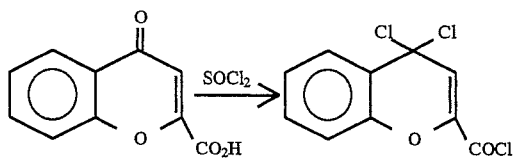

If the substituent $R^1$ or $R^2$ in the general formula (1) is a benzoylamino group substituted with an alkoxy group, there is required a step of reacting an acid halide of the general formula (12):

wherein $R^5$ is $C_1$–$C_{20}$ alkyl or aralkyl and Z is halogen, with a compound of the general formula (13):

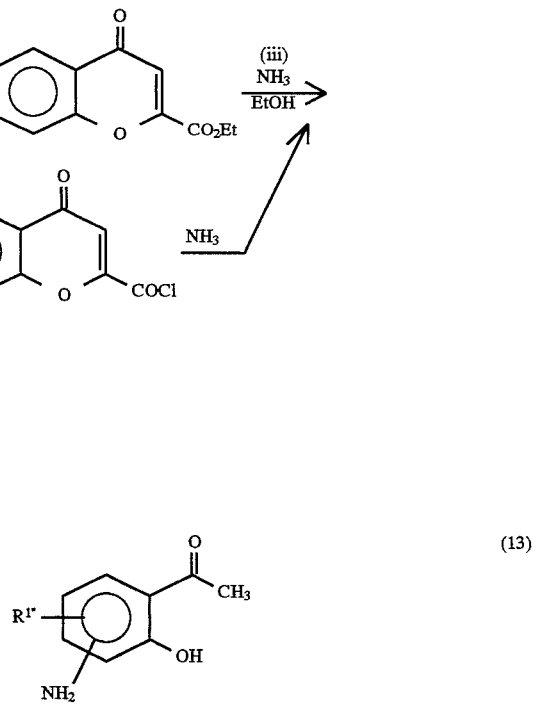

wherein $R^{1''}$ is hydrogen, halogen, hydroxy, $C_1$–$C_5$ alkoxy, nitro or amino, in the presence of a base.

In usual cases, pyridine or an aliphatic amine such as triethylamine is used as the base. If an aliphatic amine is used, there will occur a problem that a by-product may be formed by the additional acylation of the hydroxyl group of the compound (13). If pyridine is used, the above step is not always satisfactory for the production on an industrial scale because much difficulty is found in removing it from the waste water.

SUMMARY OF THE INVENTION

Under these circumstances, the present inventors have intensively studied to solve the above-described problems. As the result, they have found that the substitution of particular pyridine compounds or aromatic compounds as the solvent for pyridine or alcohol solvents used in the conventional processes makes it possible to reduce the load of waste water and to produce 2-cyano-4-oxo-4H-benzopyran compounds with high efficiency, and they further made various investigations, thereby completing the present invention.

Thus, the present invention provides a process of producing a 2-cyano-4-oxo-4H-benzopyran compound of the general formula (2):

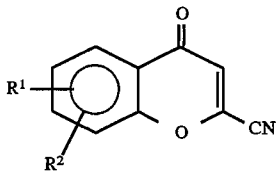
(2)

wherein $R^1$ and $R^2$ are independently hydrogen, halogen, hydroxy, lower alkyl, lower alkoxy, nitro or a group of the formula RCONH wherein R is alkyl, phenyl, phenyl-substituted alkyl, phenylalkoxyphenyl or alkoxyphenyl, characterized in that:

a carboxamide of the general formula (1):

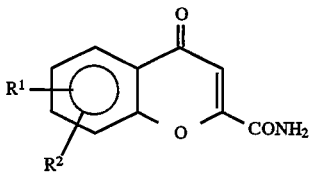
(1)

wherein $R^1$ and $R^2$ are each as defined above, is reacted with a dehydrating agent in the presence of a pyridine compound of the general formula (4):

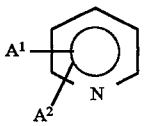
(4)

wherein $A^1$ and $A^2$ are independently hydrogen or lower alkyl.

If the final product cannot be obtained as crystals having good filtration properties by ordinary treatments, the reaction product is dissolved in an organic solvent insoluble or slightly soluble in water, and this solution is poured into water, after which the organic solvent is removed by distillation with stirring to effect the crystallization of the 2-cyano-4-oxo-4H-benzopyran compound (2).

DETAILED DESCRIPTION OF THE INVENTION

The production process of the present invention is characterized in that a carboxamide of the general formula (1) is reacted with a dehydrating agent in the presence of a pyridine compound of the general formula (4).

The following will describe this nitrile formation step.

Examples of the carboxamide (1) as the starting material used in the present invention are 2-carbamoyl-4-oxo-4H-benzopyran compounds such as 7-methyl-2-carbamoyl-4-oxo-4H-benzopyran, 8-methyl-2-carbamoyl-4-oxo-4H-benzopyran, 7-ethyl-2-carbamoyl-4-oxo-4H-benzopyran, 8-ethyl-2-carbamoyl-4-oxo-4H-benzopyran, 7-propyl-2-carbamoyl-4-oxo-4H-benzopyran, 8-propyl-2-carbamoyl-4-oxo-4H-benzopyran, 5-hydroxy-2-carbamoyl-4-oxo-4H-benzopyran, 7-hydroxy-2-carbamoyl-4-oxo-4H-benzopyran, 7-methoxy-2-carbamoyl-4-oxo-4H-benzopyran, 8-methoxy-2-carbamoyl-4-oxo-4H-benzopyran, 7-ethoxy-2-carbamoyl-4-oxo-4H-benzopyran, 8-ethoxy-2-carbamoyl-4-oxo-4H-benzopyran, 7-propoxy-2-carbamoyl-4-oxo-4H-benzopyran, 8-propoxy-2-carbamoyl-4-oxo-4H-benzopyran, 6-bromo-2-carbamoyl-4-oxo-4H-benzopyran, 8-bromo-2-carbamoyl-4-oxo-4H-benzopyran, 6-nitro-2-carbamoyl-4-oxo-4H-benzopyran, 8-nitro-2-carbamoyl-4-oxo-4H-benzopyran, 6-(3-phenyl-1-propyl)carbonylamino-2-carbamoyl-4-oxo-4H-benzopyran, 8-(3-phenyl-1-propyl)carbonylamino-2-carbamoyl-4-oxo-4H-benzopyran, 6-(4-phenyl-1-butyl)carbonylamino-2-carbamoyl-4-oxo-4H-benzopyran, 8-(4-phenyl-1-butyl)carbonylamino-2-carbamoyl-4-oxo-4H-benzopyran, 6-[4-(3-phenyl-1-propoxy)benzoyl]amino-2-carbamoyl-4-oxo-4H-benzopyran, 8-[4-(3-phenyl-1-propoxy)benzoyl]amino-2-carbamoyl-4-oxo-4H-benzopyran, 6-[4-(4phenyl-1-butoxy)benzoyl]amino-2-carbamoyl-4-oxo-4H-benzopyran and 8-[4-(4-phenyl-1-butoxy)benzoyl]amino-2-carbamoyl-4-oxo-4H-benzopyran.

The pyridine compound of the general formula (4) used in the reaction of this step preferably has lower alkyl groups of 1 to 5 carbon atoms in the positions of the substituents $A^1$ and $A^2$. Most preferred is 5-ethyl-2-methylpyridine. The pyridine compound can be used alone or as a mixture with an inert solvent to this reaction. If the pyridine compound is used alone, the amount thereof is usually 0.5 to 50 times the amount of the carboxamide (1). If the pyridine compound is used as a mixture with any other solvent, the proportion of pyridine compound in the solvent mixture is usually in the range of 1% to 99%, and the amount thereof is not particularly limited.

Examples of the solvent which can be used are hydrocarbons such as hexane, benzene, toluene and xylene; halogenated hydrocarbons such as dichloroethane; ethers such as diethyl ether and t-butyl methyl ether; and nitriles such as acetonitrile.

Examples of the dehydrating agent which can be used in this step are phosphorous pentoxide, phosphorous pentachloride, acetic anhydride, chloroformate, phosphorous oxychloride or phosgene. The amount thereof is usually in the range of 1 to 50 equivalents, preferably 1.5 to 10 equivalents, based on the carboxamide (1).

The reaction conditions are, for example, as follows: (a) the carboxamide (1) is added to the pyridine compound (4) (or its mixture with another solvent), and the dehydrating agent is then mixed therewith; (b) the dehydrating agent is added to the pyridine compound (4) (or its mixture with another solvent), and the carboxamide (1) is then mixed therewith; (c) the carboxamide (1) is added to the pyridine compound (4), and another solvent and the dehydrating agent are then mixed therewith; or (d) the dehydrating agent is added to the pyridine compound (4), and another solvent and the carboxamide (1) are then mixed therewith. There are no particular limitations in order or time for the above addition.

The reaction temperature, although it is not particularly limited, may preferably vary with the carboxamide (1). It is usually in the range of −50° to 200° C., preferably −20° to 150° C.

The reaction time is not particularly limited, and the end point of the reaction can be determined at the time when the starting material is almost completely consumed.

After completion of the reaction, it is preferred that water or aqueous alkaline solution is poured into the reaction mixture or alternatively the reaction mixture is poured into water or aqueous alkaline solution in order to decompose excess dehydrating agent.

From the reaction mass thus obtained, the desired 2-cyano-4-oxo-4H-benzopyran compound (2) can be obtained by, for example, (a) cooling and effecting its crystallization; (b) effecting its crystallization by the addition of a solvent having poor solubility; (c) effecting its crystallization by the transfer of the pyridine compound (4) into the aqueous layer using hydrochloric acid or sulfuric acid, or subjecting to extraction with another solvent; and (d) subjecting to concentration. If crystals having good filtration properties cannot be obtained by the procedures (a), (b) or (c), the following technique can provide such crystals, which has been found by the present inventors.

That is, the 2-cyano-4-oxo-4H-benzopyran compound (2) is dissolved or suspended in an organic solvent having no or poor solubility in water, and the resultant solution or suspension is poured into water with stirring, after which the organic solvent is removed by distillation while the stirring is continued, whereby crystals of the desired organic compound having slight solubility in water are deposited in water.

The organic solvent having no or poor solubility in water is not particularly limited, so long as it remains separated from water when mixed with water. Examples of such an organic solvent are hydrocarbons such as hexane, benzene, toluene and xylene; halogenated hydrocarbons such as dichloroethane; ethers such as diethyl ether and t-butyl methyl ether; and nitriles.

First, the compound (2) is dissolved or suspended in an organic solvent having no or poor solubility in water.

The temperature of this solution or suspension, although it is not particularly limited, may vary from room temperature to the boiling point of the solvent. The concentration of the compound (2) is not particularly limited, and it may conveniently be selected in the range of 0.1% to 90% by weight. If the reaction mass gives a suspension, it is preferred that the reaction mass has fluidity as a matter of course.

The solution or suspension thus obtained is then poured into water with stirring, and while the stirring is continued in such a manner that the poured solution or suspension remains dispersed in water, preferably in the form of droplets, the organic solvent is removed by distillation. The stirring blade can be a paddle blade, turbine blade, sweptback blade, bull-margin blade or the like, all of which are used in usual cases.

The amount of water is not particularly limited; however, if the organic solvent used forms an azeotropic mixture with water, the residual water has to be present in the crystallized mass when the organic solvent is completely removed by distillation.

The temperature of the crystallized mass is kept above the temperature at which the organic solvent can be removed by distillation, e.g., the boiling point of the organic solvent, or the azeotropic point if the organic solvent forms an azeotropic mixture with water.

The organic solvent can be removed by distillation under pressure or under reduced pressure, and if the organic compound used is thermally unstable, it is preferred that the organic solvent is removed under reduced pressure.

Further, a dispersing agent can be used to maintain the state that the solution or suspension remains dispersed in water.

The removal of the solvent by distillation in this way effects the crystallization, and grown crystals are deposited in water. The deposited crystals can readily be collected, for example, by filtration.

This technique makes it possible to obtain large crystals having excellent filtration properties with high efficiency.

The carboxamide (1) as the starting material used in the present invention can be obtained by the following ring formation step and the amide formation step.

The following will describe the ring formation step.

In this step, the 2-carboxy-4-oxo-4H-benzopyran compound of the general formula (3) is obtained by reacting a 2-hydroxyacetophenone compound of the general formula (5):

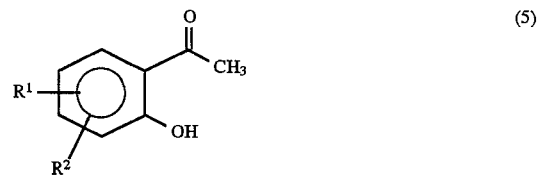

wherein $R^1$ and $R^2$ are each as defined above, with a dialkyl oxalate compound of the general formula (6):

wherein $R^3$ is lower alkyl, in the presence of an alcoholate in an aromatic compound solvent to give a compound of the general formula (7):

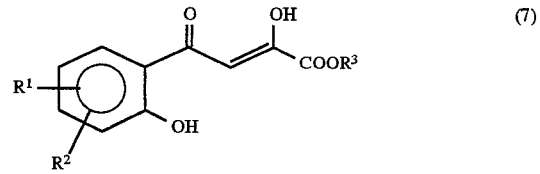

wherein $R^1$, $R^2$ and $R^3$ are each as defined above, and treating the compound (7) with an acid.

Examples of the 2-hydroxyacetophenone compound (5) which can be used in the above reaction are 3-methyl-2-hydroxyacetophenone, 4-methyl-2-hydroxyacetophenone, 3-ethyl-2-hydroxyacetophenone, 4-ethyl-2-hydroxyacetophenone, 3-propyl-2-hydroxyacetophenone, 4-propyl-2-hydroxyacetophenone, 4-methoxy-2-hydroxyacetophenone, 3-methoxy-2-hydroxyacetophenone, 4-ethoxy-2-hydroxyacetophenone, 3-ethoxy-2-hydroxyacetophenone, 4-propoxy-2-hydroxyacetophenone, 3-propoxy-2-hydroxyacetophenone, 5-bromo-2-hydroxyacetophenone, 3-bromo-2-hydroxyacetophenone, 5-nitro-2-hydroxyacetophenone, 3-nitro-2-hydroxyacetophenone, 5-(3-phenyl-1-propyl)carboxylamino-2-hydroxyacetophenone, 3-(3-phenyl-1-propyl) carbonylamino-2-hydroxyacetophenone, 5-(4-phenyl-1-butyl)carbonylamino-2-hydroxyacetophenone, 3-(4-phenyl-1-butyl)carbonylamino-2-hydroxyacetophenone, 5-[4-(3-phenyl-1-propoxy)benzoyl]amino-2-hydroxyacetophenone, 3-[4-(3-phenyl-1-propoxy)benzoyl]amino-2-hydroxyacetophenone, 5-[4-(4-phenyl-1-butoxy)benzoyl]amino-2-hydroxyacetophenone, 3-[4-(4-phenyl-1-butoxy)benzoyl]amino-2-hydroxyacetophenone and 2,4-dihydroxyacetophenone.

Examples of the alcoholate which can be used in this reaction are methylate, ethylate and sodium or potassium tertiary butoxide. These alcoholates can be used alone or in combination. These alcoholates may be used as an alcohol solution. The amount thereof is usually 2 to 10 times the mole of the 2-hydroxyacetophenone compound (5).

Examples of the dialkyl oxalate compound are diethyl oxalate and dimethyl oxalate. The amount thereof is usually 1 to 10 times the mole of the 2-hydroxyacetophenone compound (5).

Examples of the solvent which can be used in this reaction are alcohols such as methanol and ethanol; hydrocarbons such as benzene, toluene, xylene and ethylbenzene; nitrated hydrocarbons such as nitrobenzene; halogenated hydrocarbons such as chlorobenzene and dichlorobenzene; pyridine compounds such as 5-ethyl-2-methylpyridine; aliphatic hydrocarbons such as pentane, hexane and heptane; ethers such as dioxane, tetrahydrofuran and t-butyl methyl ether. Most preferred are toluene, xylene, chlorobenzene and dichlorobenzene in that these solvents increase the reactivity and reduce the load of waste water. The amount thereof, although it is not particularly limited, is preferably about 1 to 50 times the weight of the 2-hydroxyacetophenone compound (5).

The reaction temperature is usually set at 200° C. or lower, preferably –50° C. to 150° C.

The degree of reaction progress can be determined by ordinary analytical means such as liquid chromatography.

After completion of the reaction, the ring-closing reaction is effected by the addition of an acid containing no or small amounts of water, such as concentrated sulfuric acid, hydrogen chloride gas, glacial acetic acid or methanesulfonic acid, to the reaction mass. If a water-containing acid such as aqueous hydrogen chloride is used as an acid, the ester is hydrolyzed to form some impurities, which causes a decrease both in yield and quality.

The amount of acid to be used is usually 10 times or less the mole of the base used, preferably 1 to 5 times the mole of the alcoholate used. The reaction temperature is usually set at 200° C. or lower, preferably –50° to 100° C. After confirmation of the end point of the reaction by ordinary analytical means such as liquid chromatography, water is added to the reaction mass, and the mixture is subjected to separation of an organic layer, whereby the desired product can be obtained from the organic layer.

Examples of the carboxy-4-oxo-4H-benzopyran compound (3) thus obtained are 7-methyl-2-ethoxycarbonyl-4-oxo-4H-benzopyran, 8-methyl-2-ethoxycarbonyl-4-oxo-4H-benzopyran, 7-ethyl-2-ethoxycarbonyl-4-oxo-4H-benzopyran, 8-ethyl-2-ethoxycarbonyl-4-oxo-4H-benzopyran, 7-propyl-2-ethoxycarbonyl-4-oxo-4H-benzopyran, 8-propyl-2-ethoxycarbonyl-4-oxo-4H-benzopyran, 7-methoxy-2-ethoxycarbonyl-4-oxo-4H-benzopyran, 8-methoxy-2-ethoxycarbonyl-4-oxo-4H-benzopyran, 7-methoxy-2-methoxy carbonyl-4-oxo-4H-benzopyran, 8-methoxy-2-methoxycarbonyl-4-oxo-4H-benzopyran, 7-ethoxy-2-ethoxycarbonyl-4-oxo-4H-benzopyran, 8-ethoxy-2-ethoxycarbonyl-4-oxo-4H-benzopyran, 7-ethoxy-2-methoxycarbonyl-4-oxo-4H-benzopyran, 8-ethoxy-2-methoxycarbonyl-4-oxo-4H-benzopyran, 7-propoxy-2-ethoxycarbonyl-4-oxo-4H-benzopyran, 8-propoxy-2-ethoxycarbonyl-4-oxo-4H-benzopyran, 7-propoxy-2-methoxycarbonyl-4-oxo-4H-benzopyran, 8-propoxy-2-methoxycarbonyl-4-oxo-4H-benzopyran, 6-bromo-2-ethoxycarbonyl-4-oxo-4H-benzopyran, 8-bromo-2-ethoxycarbonyl-4-oxo-4H-benzopyran, 6-bromo-2-methoxycarbonyl-4-oxo-4H-benzopyran, 8-bromo-2-methoxycarbonyl-4-oxo-4H-benzopyran, 6-nitro-2-ethoxycarbonyl-4-oxo-4H-benzopyran, 8-nitro-2-ethoxycarbonyl-4-oxo-4H-benzopyran, 6-nitro-2-methoxycarbonyl-4-oxo-4H-benzopyran, 8-nitro-2-methoxycarbonyl-4-oxo-4H-benzopyran, 6-(3-phenyl-1-propyl)-carbonylamino-2-ethoxycarbonyl-4-oxo-4H-benzopyran, 8-(3-phenyl-1-propyl)carbonylamino-2-ethoxycarbonyl-4-oxo-4H-benzopyran, 6-(3-phenyl-1-propyl)carbonylamino-2-methoxycarbonyl-4-oxo-4H-benzopyran, 8-(3-phenyl-1-propyl)carbonylamino-2-methoxycarbonyl-4-oxo-4H-benzopyran, 6-(4-phenyl-1-butyl)carbonylamino-2-ethoxycarbonyl-4-oxo-4H-benzopyran, 8-(4-phenyl-1-butyl)carbonylamino-2-ethoxycarbonyl-4-oxo-4H-benzopyran, 6-(4-phenyl-1-butyl)carbonylamino-2-methoxycarbonyl-4-oxo-4H-benzopyran, 8-(4-phenyl-1-butyl)carbonylamino-2-methoxycarbonyl-4-oxo-4H-benzopyran, 6-[4-(3-phenyl-1-propoxy)benzoyl]amino-2-ethoxycarbonyl-4-oxo-4H-benzopyran, 8-[4-(3-phenyl-1-propoxy)benzoyl]amino-2-ethoxycarbonyl-4-oxo-4H-benzopyran, 6-[4-(3-phenyl-1-propoxy)benzoyl]amino-2-methoxycarbonyl-4-oxo-4H-benzopyran, 8-[4-(3-phenyl-1-propoxy)benzoyl]amino-2-methoxycarbonyl-4-oxo-4H-benzopyran, 6-[4-(4-phenyl-1-butoxy)benzoyl]amino-2-ethoxycarbonyl-4-oxo-4H-benzopyran, 8-[4-(4-phenyl-1-butoxy)benzoyl]amino-2-ethoxycarbonyl-4-oxo-4H-benzopyran, 6-[4-(4-phenyl-1-butoxy)benzoyl]amino-2-methoxycarbonyl-4-oxo-4H-benzopyran, 8-[4-(4-phenyl-1-butoxy)benzoyl]amino-2-methoxycarbonyl-4-oxo-4H-benzopyran, 6-[4-(4-phenyl-1-butoxy)benzoyl]amino-2-isopropoxycarbonyl-4-oxo-4H-benzopyran, 8-[4-(4-phenyl-1-butoxy)benzoyl]amino-2-isopropoxycarbonyl-4-oxo-4H-benzopyran and 7-hydroxy-2-methoxycarbonyl-4-oxo-4H-benzopyran.

The following will describe the amide formation step.

The 2-carboxy-4-oxo-4H-benzopyran compound (3) obtained in the foregoing ring formation step is then reacted with ammonia in the presence of a pyridine compound of the general formula (4) to give a carboxamide of the general formula (1).

In this step, a pyridine compound of the general formula (4) is used as the solvent, and an alcohol such as methanol, ethanol, isopropyl alcohol and tertiary butanol is used as a co-solvent for dissolving ammonia. The pyridine compound can be used alone or as a mixture with any other solvent such as ethers such as dioxane, tetrahydro-furan and diglyme; hydrocarbons such as benzene, toluene, xylene and hexane; and halogenated hydrocarbons such as chlorobenzene, chloroform and 1,2-dichloroethane.

The pyridine compound (4) may optionally be substituted with alkyl of 1 to 5 carbon atoms. Most preferred are pyridine and 5-ethyl-2-methylpyridine. The amount thereof, although it is not particularly limited, is preferably about 1 to 50 times the amount of 2-carboxy-4-oxo-4H-benzopyran compound (3).

In this reaction, liquid ammonia or ammonia gas is used as the nucleophilic reagent. The amount thereof is about 1 to 30 times, preferably about 1 to 10 times, the mole of the 2-carboxy-4-oxo-4H-benzopyran compound (3).

The reaction temperature is usually set at 200° C. or lower, preferably –50° C. to 150° C.

The degree of reaction progress can be determined by ordinary analytical means such as liquid chromatography.

After completion of the reaction, for example, excess ammonia is removed and recovered as a gas or its alcohol solution by increasing the temperature, whereby the desired product can be obtained from the residue. At that time, if part of the desired product is further reacted with additional one ammonia molecule to give a ring-opened compound, the treatment with a sulfonic acid compound such as methanesulfonic acid, trifluoromethanesulfonic acid or para-toluenesulfonic acid can make the ring-closing reaction proceed, whereby the desired carboxamide (1) can be obtained in high yield.

The amount of sulfonic acid compound to be used is usually about 0.1 to 10 equivalents, preferably about 0.5 to 3 equivalents, based on the starting 2-carboxy-4-oxo-4H-benzopyran compound (3).

The reaction temperature is usually set at 200° C. or lower, preferably 50° to 150° C.

The degree of reaction progress can be determined by ordinary analytical means such as liquid chromatography.

After completion of the reaction, the reaction mixture is cooled, and the desired product can be obtained therefrom in the form of crystals having excellent filtration properties by the addition of methanol and then filtration. Since the ammonium salts of the sulfonic acid compound which have been formed by the reaction transfer to the filtrate, methanol and pyridine compound (4) can be recovered for recycling by distillation without washing with water to remove the salts from the desired products.

If the 2-hydroxyacetophenone compound of the general formula (5) has a benzoylamino group substituted with at least one alkoxy group, it is produced in accordance with the following scheme:

That is, a phenol derivative of the general formula (8):

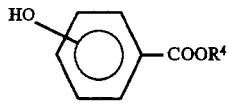

wherein $R^4$ is $C_1$–$C_5$ alkyl, is reacted with an alkylating agent of the general formula (9):

 (9)

wherein X is halogen and $R^5$ is $C_1$–$C_{20}$ alkyl or aralkyl, in the presence of a basic substance to give an ether compound of the general formula (10):

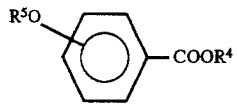

wherein $R^4$ and $R^5$ are each as defined above; the compound (10) is then hydrolyzed in the presence of a base to give a carboxylic acid derivative of the general formula (11):

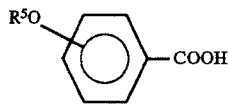

wherein $R^5$ is as defined above; the carboxylic acid derivative (11) is then reacted with a halogenating agent to give an acid halide of the general formula (12):

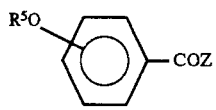

wherein $R^5$ is as defined above and Z is halogen; the resultant acid halide (12) is reacted with a compound of the general formula (13):

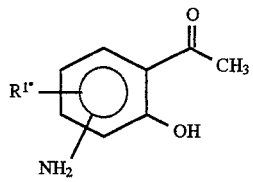

wherein $R^{1''}$ is hydrogen, halogen, hydroxy, $C_1$–$C_5$ alkoxy, nitro or amino, in the presence of a metal hydroxide, carbonate, hydrogencarbonate or a pyridine compound of the general formula (4) as a dehydrohalogenation agent to give a compound of the general formula (5a):

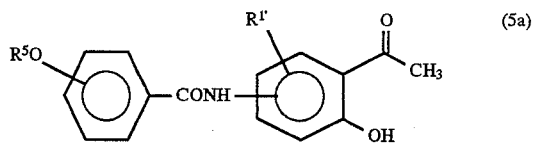

wherein $R^{1'}$ is hydrogen, halogen, hydroxy, $C_1$–$C_5$ alkoxy, nitro or a group of the formula:

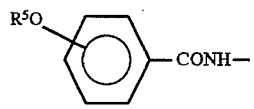

wherein $R^5$ is as defined above.

Examples of the substituent $R^4$ in the phenyl derivative (8) used in the above reaction are methyl, ethyl, propyl, butyl and pentyl. Examples of the substituent $R^5$ in the alkylating agent (9) are methyl, ethyl, propyl, butyl, pentyl, hexyl, heptyl, octyl, nonyl, decyl, benzyl, phenetyl, phenylbutyl, phenylpentyl, phenylhexyl, phenylheptyl, phenylnonyl, phenylnonyl and phenyldecyl. The above methylene chain may optionally be branched and the above phenyl group may optionally be substituted with halogen.

The alkylation as the first step of the above reaction route is effected in the presence of a basic substance, typical examples of which are alkali metal hydrides such as sodium hydride and potassium hydride; alkali metal alcoholates such as sodium ethylate and sodium methylate; and alkali metal carbonates such as sodium carbonate and potassium carbonate.

The amount thereof should be one equivalent or more, based on the phenol derivative (8), and it is usually in the range of 1 to 5 equivalents, although the upper limit thereof is not particularly limited.

Examples of the reaction solvent are inert solvents to the reaction, such as tetrahydrofuran, diethyl ether, acetone, methyl ethyl ketone, methyl isobutyl ketone, toluene, benzene, chlorobenzene, dichloromethane, dichloroethane, chloroform, carbon tetrachloride, hexane, dimethylformamide, dimethylsulfoxide, hexamethylphosphorylamide and N-methylpyrrolidone. These solvents can be used alone or in combination. Most preferred is methyl isobutyl ketone. The amount of solvent to be used is not particularly limited.

The reaction temperature is usually set at −50° to 120° C., preferably −30° to 100° C.

The end point of the derivative (8) is almost completely the phenol derivative (8) is almost completely consumed.

After completion of the reaction, the reaction mixture is subjected to hydrolysis by the addition of water and alkali. Examples of the alkali which can be used are inorganic bases such as sodium hydroxide, potassium hydroxide, sodium carbonate, potassium carbonate, sodium hydrogencarbonate and potassium hydrogencarbonate; and organic bases such as 1,8-diazabicyclo[5.4.0]undec-7-ene. The amount thereof is usually one time or more, preferably 10 times or less, the equivalent of the ester derivative (10).

The reaction temperature is usually set at −30° to 200° C., preferably −20° to 150° C. The end point of the reaction can be determined at the time when the ester derivative (10) is almost completely consumed.

After completion of the reaction, the reaction mixture is subjected to usual work up such as separation of an aqueous layer, followed by deposition with an acid and extraction, and the resultant carboxylic acid derivative (11) is halogenated with a halogenating agent such as thionyl chloride or phosphorous oxychloride to give a compound of the general formula (12). Then the compound (12) is reacted with an amino-containing compound of the general formula (13) in the presence of a base. Examples of the base are inorganic salts such as sodium hydroxide, sodium carbonate and sodium hydrogencarbonate; and pyridine compounds of the general formula (4). Preferred are inorganic salts or 5-ethyl-2-methylpyridine. If an inorganic salt is used, the presence of water may be allowed in the reaction system.

The reaction is effected in the presence of a solvent. Examples of the solvent which can be used are inert solvents to the reaction, such as tetrahydrofuran, diethyl ether, acetone, methyl ethyl ketone, methyl isobutyl ketone, toluene, benzene, chloro-benzene, dichloromethane, dichloroethane, chloroform, carbon tetrachloride, hexane, dimethylformamide, dimethylsulfoxide, hexamethylphosphorylamide and N-methylpyrrolidone. These solvents can be used alone or in combination. Most preferred is toluene. The amount of solvent to be used is not particularly limited.

The reaction temperature is usually set at −80° to 200° C., preferably −30° to 100° C.

The end point of the reaction can be determined at the time when the compound of the general formula (12) or (13) is almost completely consumed.

After completion of the reaction, the reaction mixture is subjected to usual work up such as separation of an organic layer, whereby the desired product can be obtained. The crude product can be used in the subsequent step without any purification for certain reasons on the facilities for production or can be purified by ordinary procedures such as crystallization to isolate the desired product. In case where the desired product is obtained without isolating its intermediate, such a process is favorable for the production on an industrial scale.

According to the present invention, it is possible to produce 2-cyano-4-oxo-4H-benzopyran compounds with high efficiency while reducing the formation of waste matters such as waste water to the utmost. Further, even in case where the desired product has poor filtration properties in the ordinary crystallization, the crystal formation technique of the present invention can make it possible to obtain large crystals having good filtration properties.

The present invention will be further illustrated by way of the following examples, which are not to be construed to limit the scope thereof.

Production Example 1

Production of 4-(4-phenyl-1-butoxy)benzoic acid

To 100 ml of methyl isobutyl ketone were added 17.6 g of methyl p-hydroxybenzoate, 23.0 g of 4-phenyl-1-bromobutane and 22 g of anhydrous potassium carbonate. The mixture was heated under reflux for 10 hours for the reaction, after which 65 g of 20% sodium hydroxide was added thereto. The mixture was heated under reflux for 6 hours for the reaction. After completion of the reaction, 300 ml of water was added thereto.

The reaction mixture was separated into an aqueous layer and an organic layer. After removal of the organic layer, the aqueous layer was washed twice with 50 ml of toluene. The resultant aqueous layer was made acidic by the addition of 48% sulfuric acid, and then extracted with 200 ml of toluene, which afforded a solution of 4-(4-phenyl-1-butoxy)benzoic acid in toluene. The product content in the solution was measured and the yield was determined to be 93%.

Production Example 2

Production of 3[4-(4-phenyl-1-butoxy)benzoyl]amino-2-hydroxyacetophenone

To the solution of 4-(4-phenyl-1-butoxy)benzoic acid in toluene obtained in Production Example 1, 12.9 g of thionyl chloride was added dropwise at room temperature, and the mixture was stirred at 40° C. for 30 minutes. After completion of the reaction, excess thionyl chloride and toluene were removed under reduced pressure, which afforded 4-(4-phenyl-1-butoxy)benzoyl chloride. This solution and 52.1 g of 10% aqueous sodium carbonate (pure content, 5.21 g) were simultaneously added dropwise to a mixture containing 18.5 g of 3-amino-2-hydroxyacetophenone hydrochloride and 50 ml of toluene at a temperature of 45°±5° C. while the pH was kept to 7 or less. The reaction mixture was kept at the same temperature for about 3 hours. After completion of the reaction, the reaction mixture was subjected to separation of an organic layer, which afforded a solution of 3-[(4-phenyl-1-butoxy)benzoyl]amino-2-hydroxyacetophenone in toluene. The product content in the solution was measured and the yield was determined to be 98%.

It is also possible to obtain 38.5 g of 3-[(4-phenyl-1-butoxy)benzoyl]amino-2-hydroxyacetophenone as crystals by concentration of the above toluene solution and subsequent addition of hexane (yield 97%).

Production Example 3

Production of 8-[4-(4-phenyl-1-butoxy)benzoyl]amino-2-ethoxycarbonyl-4-oxo-4H-benzopyran In a mixture containing 180 g of toluene and 12.0 g of diethyl oxalate was dissolved 25.0 g of 3-(4-phenyl-1-butoxy)benzoylamino-2-hydroxyacetophenone, to which 62.0 g of a 20% solution of sodium ethylate in ethanol was added dropwise at 50° C. After completion of the reaction, 12.6 g of 98% sulfuric acid was subsequently added, and the mixture was stirred at 60° C. for 0.5 hours. Then, 140 g of water was added, and the mixture was subjected to separation of an organic layer. The resultant organic layer was concentrated, after which 54.0 g of hexane was added, and the mixture was filtered below 10° C., which afforded 29.2 g of 8-[4-(4-phenyl-1-butoxy) benzoyl]-amino-2-ethoxycarbonyl-4-oxo-4H-benzopyran.

Production Example 4

Production of 8-[4-(4-phenyl-1-butoxy)benzoyl]amino-2-carbamoyl-4-oxo-4H-benzopyran To a mixture containing 120 ml of 5-ethyl-2-methylpyridine and 75 ml of methanol was added 29.5 g of 8-[4-(4-phenyl-1-butoxy)benzoyl]amino-2-ethoxycarbonyl-4-oxo-4H-benzopyran, into which 8.2 g of ammonia gas was bubbled around 0° C., and the mixture was stirred below 30° C. for 3 hours. Then, the temperature was increased to 80° C., and excess ammonia and part of the methanol were removed and recovered into methanol in another vessel. The recovered ammonia and/or methanol can be used again in the subsequent production. The temperature was increased to 80° C., and the remaining methanol and part of 5-ethyl-2-methylpyridine were removed by reducing a pressure down to 30 mmHg. Subsequently, 60.8 mmol (5.84 g) of methane sulfonic acid was added, and the mixture was stirred at 100° C. for 6 hours. Then, the temperature was decreased to 60° C., and methanol was added dropwise at 50° to 60° C. The mixture Was cooled to 0° C., and the deposited crystals were collected by filtration, which afforded 27.7 g of 8-[4-(4-phenyl-1-butoxy)benzoyl]amino-2-carbamoyl-4-oxo-4H-benzopyran (yield 99%).

EXAMPLE 1

Production of 8-[4-(4-phenyl-1-butoxy)benzoyl]amino-2-cyano4-oxo-4H-benzopyran

To a mixture containing 50 g of 5-ethyl-2-methylpyridine and 50 g of toluene was added 10 g of 8-[4-(4-phenyl-1-butoxy)benzoyl]amino-2-carbamoyl-4-oxo-4H-benzopyran, and the reaction was allowed to proceed at 60° C. for 6 hours. After completion of the reaction, 400 ml of 4N hydrochloric acid was added, and the mixture was extracted with 400 ml of toluene. The extract was washed with diluted hydrochloric acid, water and aqueous sodium hydrogencarbonate, and the organic layer was concentrated under reduced pressure, which afforded 8.4 g of 8-[4-(4-phenyl-1-butoxy) benzoyl]amino-2-cyano-4-oxo-4H-benzopyran as a pale brown product (yield 88%).

Comparative Example 1

The reaction was effected in the same manner as described in Example 1, except that pyridine was used in place of 5-ethyl-2-methylpyridine.

The reaction mixture became like dark brown tar and it was therefore impossible to isolate the desired product.

EXAMPLE 2

Preparation of 8-[4-(4-phenyl-1-butoxy)benzoyl]amino-2-cyano-4-oxo-4H-benzopyran crystals In a 2.5-L separable flask equipped with a stirring machine having three swept-back blades, 1600 ml of water was placed and stirred at 1200 rpm while being kept at 98° C. Then, 11.0 g of 8-[4-(4-phenyl-1-butoxy)benzoyl]amino-2-cyano-4-oxo-4H-benzopyran was dissolved in 300 g of toluene kept at 80° C., and the resultant solution was poured into the separable flask over about 3 hours, at which time an azeotropic mixture of toluene and water was removed by distillation while the temperature of the system was being kept at 97° to 99° C. Just after completion of the addition, the distillation of toluene was completed, and crystals were deposited in water. The separable flask was cooled, and the crystals were collected by filtration and dried. The filtration for several seconds gave 8-[4-(4-phenyl-1-butoxy)benzoyl] amino-2-cyano-4-oxo-4H-benzopyran crystals having a mean particle diameter of 1.1 mm.

Comparative Example 2

A toluene solution having the same composition as described in Example 2 was prepared and cooled to 0° C. with stirring at 1200 rpm, whereby crystals of 8-[4-(4-phenyl-1-butoxy)benzoyl]amino-2-cyano-4-oxo-4H-benzopyran were deposited over about 4 hours. These crystals were then treated in the same manner as described in Example 2. The crystals had poor filtration properties and the filtration time per unit volume was about 100-fold longer than the case of Example 2. The resultant crystals of 8-[4-(4-Phenyl-1-butoxy)benzoyl]amino-2-cyano-4-oxo-4H-benzopyran had a mean particle diameter of 10 μm.

EXAMPLE 3

Production of 8-nitro-2-cyano-4-oxo-4H-benzopyran

In this example, 7.8 g of 8-nitro-2-cyano-4-oxo-4H-benzopyran was produced in the same manner as described in Example 1, except that 8-nitro-2-carbamoyl-4-oxo-4H-benzopyran was used in place of 8-[4-(4-phenyl-1-butoxy) benzoyl]amino-2-carbamoyl-4-oxo-4H-benzopyran (yield 84%).

Production Example 5

Production of 8-nitro-2-methoxycarbonyl-4-oxo-4H-benzopyran

In this example, 33.0 g of 8-nitro-2-methoxycarbonyl-4-oxo-4H-benzopyran was produced in the same manner as described in Production Example 3, except that 3-nitro-2-hydroxyacetophenone, dimethyl oxalate and a 28% solution of sodium methylate in methanol were used in place of 3-(4-phenyl-1-butoxy) benzoylamino-2-hydroxyacetophenone, diethyl oxalate and a 20% solution of sodium ethylate in ethanol, respectively (yield 96%).

Production Example 6

Production of 8-nitro-2-carbamoyl-4-oxo4H-benzopyran

In this example, 26.6 g of 8-nitro-2-carbamoyl-4-oxo-4H-benzopyran was produced in the same manner as described in Production Example 4, except that 8-nitro-2-methoxycarbonyl-4-oxo-4H-benzopyran was used in place of 8-[4-(4-phenyl-1-butoxy)-benzoyl]amino-2-ethoxycarbonyl-4-oxo-4H-benzopyran (yield 96%).

EXAMPLE 4

Production of 6-nitro-2-cyano-4-oxo-4H-benzopyran

In this example, 7.9 g of 6-nitro-2-cyano-4-oxo-4H-benzopyran was produced in the same manner as described in Example 1, except that 6-nitro-2-carbamoyl-4-oxo-4H-benzopyran was used in place of 8-[4-(4-phenyl-1-butoxy) benzoyl]amino-2-carbamoyl-4-oxo-4H-benzopyran (yield 86%).

Production Example 7

Production of 6-nitro-2-methoxycarbonyl-4-oxo-4H-benzopyran

In this example, 33.0 g of 6-nitro-2-methoxycarbonyl-4-oxo-4H-benzopyran was produced in the same manner as described in Production Example 3, except that 5-nitro-2-hydroxyacetophenone, dimethyl oxalate and a 28% solution of sodium methylate in methanol were used in place of 3-(4-phenyl-1-butoxy)benzoylamino-2-hydroxyacetophenone, diethyl oxalate and a 20% solution of sodium ethylate in ethanol, respectively (yield 96%).

Production Example 8

Production of 6-nitro-2-carbamoyl-4-oxo-4H-benzopyran

In this example, 26.9 g of 6-nitro-2-carbamoyl-4-oxo-4H-benzopyran Was produced in the same manner as described in Production Example 4, except that 6-nitro-2-methoxycarbonyl-4-oxo-4H-benzopyran was used in place of 8-[4-(4-phenyl-1-butoxy)-benzoyl]amino-2-ethoxycarbonyl-4-oxo-4H-benzopyran (yield 97%).

What is claimed is:

1. A process of producing a 2-cyano-4-oxo-4H-benzopyran compound of the general formula (2):

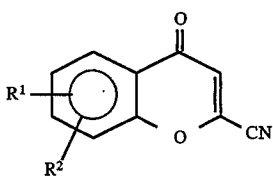
(2)

wherein $R^1$ is hydrogen, halogen, hydroxy, $C_1$–$C_5$ alkyl, $C_1$–$C_5$ alkoxy, nitro or a group of the formula RCONH wherein R is $C_1$–$C_{20}$ alkyl, phenyl, phenyl-substituted $(C_1$–$C_{20})$alkyl, phenyl($C_1$–$C_{20}$)alkoxyphenyl or $(C_1$–$C_{20})$ alkoxyphenyl, and $R^2$ is a group of said formula RCONH, said process comprising:

reacting a 2-carboxy-4-oxo-4H-benzopyran compound of the general formula

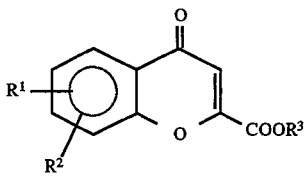
(3)

wherein $R^1$ and $R^2$ are each as defined above and $R^3$ is $C_1$–$C_5$ alkyl, with ammonia in the presence of an alcohol and a pyridine compound of the general formula (4):

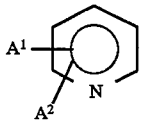
(4)

wherein $A^1$ and $A^2$ are independently hydrogen or $C_1$–$C_5$ alkyl, to give a carboxamide of the general formula (1):

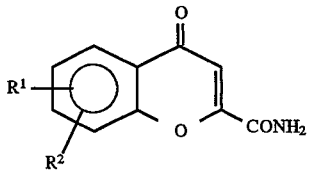
(1)

wherein $R^1$ and $R^2$ are each as defined above:

and then reacting the carboxamide (1) with a dehydrating agent in the presence of the pyridine compound (4).

2. A process according to claim 1, further comprising: dissolving the reaction product in an organic solvent insoluble or slightly soluble in water; pouring the resultant solution into water; and removing the organic solvent by distillation with stirring to effect the crystallization of the 2-cyano-4-oxo-4H-benzopyran compound (2).

3. A process according to claim 1, wherein the carboxamide of the general formula (1) is obtained by reacting a 2-hydroxyacetophenone compound of the general formula (5):

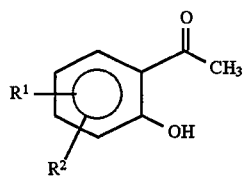
(5)

wherein $R^1$ and $R^2$ are each as defined above, with a dialkyl oxalate compound of the general formula (6):

$(COOR^3)_2$ (6)

wherein $R^3$ is $C_1$–$C_5$ alkyl, in the presence of an alcoholate in an aromatic compound solvent to give a compound of the general formula (7):

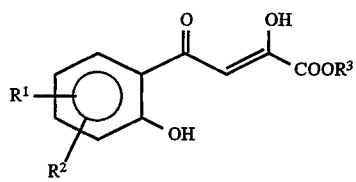
(7)

wherein $R^1$, $R^2$ and $R^3$ are each as defined above; treating the compound (7) with an acid to give the 2-carboxy-4-oxo-4H-benzopyran compound of the general formula (3); and reacting the resultant compound (3) with ammonia in the presence Of a lower alcohol and a pyridine compound of the general formula (4), followed by treatment with an acid.

4. A process according to claim 1, wherein the 2-cyano-4-oxo-4H-benzopyran compound of the general formula (2) has an alkoxybenzoylamino group in the position of the substituent $R^2$ and the carboxamide of the general formula (1) is obtained by reacting a phenol derivative of the general formula (8):

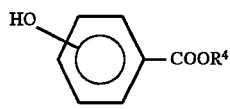
(8)

wherein $R^4$ is $C_1$–$C_5$ alkyl, with an alkylating agent of the general formula (9):

$R^5$-X (9)

wherein X is halogen and $R^5$ is $C_1$–$C_{20}$ alkyl or aralkyl, in the presence of a basic substance to give an ether compound of the general formula (10):

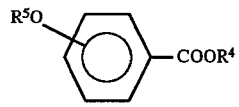
(10)

wherein $R^4$ and $R^5$ are each as defined above; hydrolyzing the compound (10) in the presence of a base to give a carboxylic acid derivative of the general formula (11):

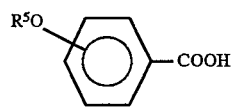
(11)

wherein $R^5$ is as defined above; reacting the carboxylic acid derivative (11) with a halogenating agent to give an acid halide of the general formula (12):

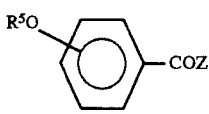

wherein $R^5$ is as defined above and Z is halogen; reacting the resultant acid halide (12) and a compound of the general formula (13):

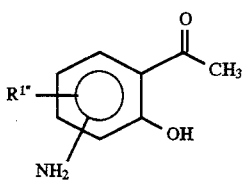

wherein $R^{1''}$ is hydrogen, halogen, hydroxy, $C_1$–$C_5$ alkoxy, nitro or amino, in the presence of a metal halide, carbonate, hydrogencarbonate or a pyridine compound of the general formula (4) as a dehydrohalogenation agent to give a compound of the general formula (5a):

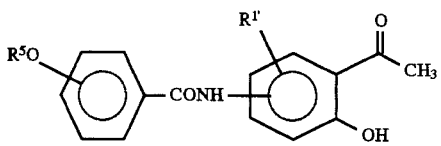

wherein $R^{1''}$ is hydrogen, halogen, hydroxy, $C_1$–$C_5$ alkoxy, nitro or a group of the formula:

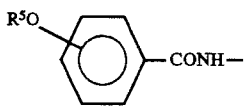

wherein $R^5$ is as defined above; reacting the resultant compound (5a) with a dialkyl oxalate compound (6) in the presence of an alcoholate in an aromatic compound solvent to give a compound of the general formula (7a):

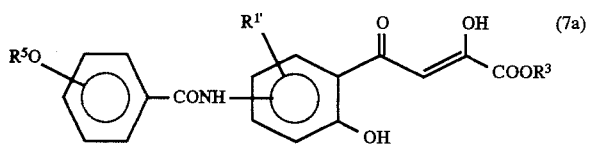

wherein $R^{1'}$ and $R^3$ are each as defined above; treating the compound (7a) with an acid to give a 2-carboxy-4-oxo-4H-benzopyran compound (3a) of the general formula (3a):

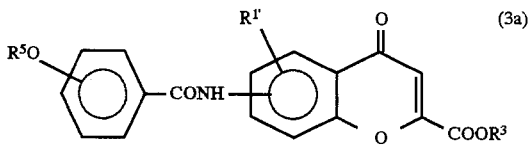

wherein $R^{1'}$ and $R^3$ are each as defined above; and reacting the resultant compound (3a) with ammonia in the presence of a lower alcohol and a pyridine compound of the general formula (4), followed by treatment with an acid.

5. A process according to claim 1, wherein the pyridine compound of the general formula (4) is 5-ethyl-2-methylpyridine.

6. A process according to claim 1, wherein the 2-cyano-4-oxo-4H-benzo-pyran compound of the general formula (2) has a nitro or RCONH group in at least one position of the substituents $R^1$ and $R^2$.

7. A process according to claim 1, wherein the 2-cyano-4-oxo-4H-benzo-pyran compound of the general formula (2) is 8-[4-(4-phenyl-1-butoxy)benzoyl]amino-2-cyano-4-oxo-4H-benzopyran, 8-nitro-2-cyano-4-oxo-4H-benzopyran or 6-nitro-2-cyano-4-oxo-4H-benzopyran.

8. A process according to claim 6, wherein the 2-cyano-4-oxo-4H-benzopyran compound of the general formula (2) has a RCONH group in at least one position of the substituents $R^1$ and $R^2$.

9. A process according to claim 8, wherein the RCONH group is positioned at the 8th position of the 2-cyano-4-oxo-4H-benzopyran compound of the general formula (2).

10. A process of producing a carboxamide of the general formula (1):

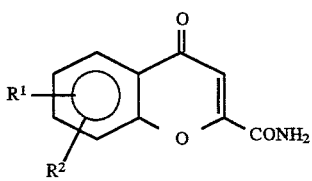

wherein $R^1$ [and $R^2$ are independently] is hydrogen, halogen, hydroxy, $C_1$–$C_5$ alkyl, $C_1$–$C_5$ alkoxy, nitro or a group of the formula RCONH wherein R is $C_1$–$C_{20}$ alkyl, phenyl, phenyl-substituted ($C_1$–$C_{20}$)alkyl, phenyl ($C_1$–$C_{20}$) alkylphenyl or ($C_1$–$C_{20}$)alkoxyphenyl, $R^2$ is a group of said formula RCONH, and $R^3$ is $C_1$–$C_5$ alkyl, said process comprising:

reacting a 2-carboxy-4-oxo-4H-benzopyran compound of the general formula (3):

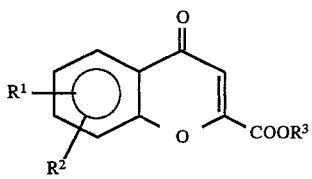

wherein $R^1$ and $R^2$ are each as defined above and $R^3$ is $C_1$–$C_5$ alkyl, with ammonia in the presence of an alcohol and a pyridine compound of the general formula (4):

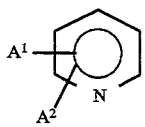

wherein $A^1$ and $A^2$ are independently hydrogen or $C_1$–$C_5$ alkyl.

11. A process according to claim 10, wherein the 2-cyano-4-oxo-4H-benzopyran compound of the general formula (2) has a nitro or RCONH group in at least one position of the substituents $R^1$ and $R^2$.

12. A process according to claim 11, wherein the 2-cyano-4-oxo-4H-benzopyran compound of the general formula (2) has a RCONH group in at least one position of the substituents $R^1$ and $R^2$.

13. A process according to claim 12, wherein the RCONH group is positioned at the 8th position of the 2-cyano-4-oxo-4H-benzopyran compound of the general formula (2).

* * * * *